United States Patent
Hatakenaka

(10) Patent No.: US 12,207,912 B2
(45) Date of Patent: Jan. 28, 2025

(54) MAGNETIC RESONANCE IMAGING APPARATUS AND ILLUMINATION CONTROL METHOD

(71) Applicant: CANON MEDICAL SYSTEMS CORPORATION, Otawara (JP)

(72) Inventor: Hiroyuki Hatakenaka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 122 days.

(21) Appl. No.: 18/066,590

(22) Filed: Dec. 15, 2022

(65) Prior Publication Data

US 2023/0190130 A1 Jun. 22, 2023

(30) Foreign Application Priority Data

Dec. 16, 2021 (JP) .................. 2021-204442

(51) Int. Cl.
*A61B 5/055* (2006.01)
*A61B 5/00* (2006.01)

(52) U.S. Cl.
CPC ............ *A61B 5/055* (2013.01); *A61B 5/0037* (2013.01)

(58) Field of Classification Search
CPC .............................. A61B 5/055; A61B 5/0037
See application file for complete search history.

(56) References Cited

U.S. PATENT DOCUMENTS

| | | | |
|---|---|---|---|
| 2017/0168124 A1 | 6/2017 | Ueda et al. | |
| 2023/0126963 A1* | 4/2023 | Litvin | A61B 6/032 600/428 |

FOREIGN PATENT DOCUMENTS

JP  2017-104401 A  6/2017

* cited by examiner

*Primary Examiner* — Gerald Johnson
(74) *Attorney, Agent, or Firm* — Oblon, McClelland, Maier & Neustadt, L.L.P.

(57) ABSTRACT

A magnetic resonance imaging apparatus according to an embodiment includes a gantry, a first illuminating unit, and processing circuitry. The gantry has a hollow bore. The first illuminating unit illuminates the hollow bore. The processing circuitry identifies the position of a predetermined region of the subject inside the hollow bore, and controls the illumination state of the first illuminating unit based on the identified position of the predetermined region.

9 Claims, 5 Drawing Sheets

MAGNETIC RESONANCE IMAGING APPARATUS AND ILLUMINATION CONTROL METHOD

CROSS-REFERENCE TO RELATED APPLICATIONS

This application is based upon and claims the benefit of priority from Japanese Patent Application No. 2021-204442, filed on Dec. 16, 2021; the entire contents of which are incorporated herein by reference.

FIELD

Embodiments described herein relate generally to a magnetic resonance imaging apparatus and an illumination control method.

BACKGROUND

In the embodiment disclosed in the present written description and the drawings, one of the problems to be solved is about appropriately controlling the illumination in a hollow bore of a gantry. However, that is not the only problem to be solved in the embodiment disclosed in the present written description and the drawings. That is, the problems corresponding to the effects attributed to the configuration explained below in the embodiment can be treated as other problems.

DETAILED DESCRIPTION

Figure 1:
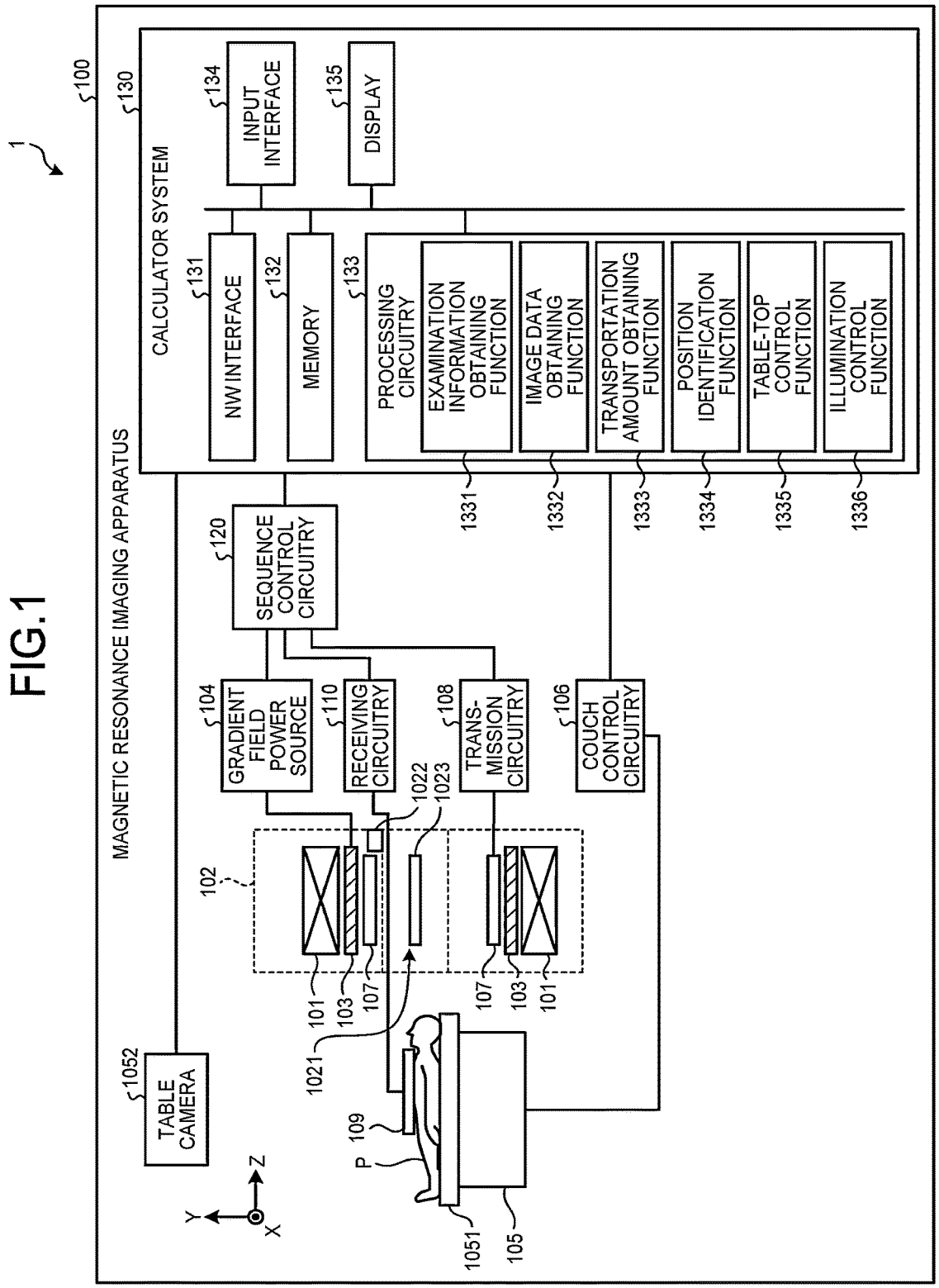
FIG. 1 is a block diagram illustrating an example of a magnetic resonance imaging apparatus according to an embodiment.

An exemplary embodiment of a magnetic resonance imaging apparatus and an illumination control method is described below with reference to the accompanying drawings. In the embodiment described below, the constituent elements referred to by the same reference numerals are assumed to perform identical operations, and the relevant explanation is not given repeatedly.

First Embodiment

FIG. 1 is a block diagram illustrating an example of a magnetic resonance imaging (MRI) apparatus 100 according to an embodiment. As illustrated in FIG. 1, the magnetic resonance imaging apparatus 100 includes a static magnetic field magnet 101, a gantry 102, a static magnetic field power source (not illustrated), a gradient coil 103, a gradient field power source 104, a table 105, table control circuitry 106, a whole-body radio frequency (RF) coil 107, transmission circuitry 108, a topical RF coil 109, receiving circuitry 110, sequence control circuitry 120, and a calculator system 130.

The configuration illustrated in FIG. 1 is only exemplary. Alternatively, for example, the constituent elements of the sequence control circuitry 120 and the calculator system 130 can be appropriately integrated or separated. Moreover, the magnetic resonance imaging apparatus 100 can include some other configurations too. Meanwhile, a subject P (for example, a human being) is not a part of the magnetic resonance imaging apparatus 100.

The X-axis, the Y-axis, and the Z-axis illustrated in FIG. 1 constitute the apparatus coordinate system specific to the magnetic resonance imaging apparatus 100. For example, the Z-axis direction is coincident with the axial direction of the cylinder hollow of the gradient coil 103, and is set to run along the magnetic flux of the electrostatic magnetic field generated due to the static magnetic field magnet 101. Moreover, the Z-axis direction is aligned in the same direction as the longitudinal direction of the table 105 and in the same direction as the craniocaudal direction of the subject P who is asked to lie down on the table 105. The X-axis direction is set along the horizontal direction that is orthogonal to the Z-axis direction. The Y-axis direction is set along the vertical direction that is orthogonal to the Z-axis direction.

The static magnetic field magnet 101 is a magnet formed in a substantially cylindrical shape of a hollow bore 1021, and generates a static magnetic field in its internal space. The static magnetic field magnet 101 is, for example, a superconducting magnet that receives the supply of an electric current from the static magnetic field power source and becomes energized. Thus, the static magnetic field power source supplies an electric current to the static magnetic field magnet 101. As another example, the static magnetic field magnet 101 can be a permanent magnet. In that case, the magnetic resonance imaging apparatus 100 need not include the static magnetic field power source. Meanwhile, it is also possible to have the static magnetic field power source installed separately from the magnetic resonance imaging apparatus 100.

The gantry 102 has the hollow bore 1021 formed in a substantially cylindrical shape; and has the static magnetic field magnet 101, the gradient coil 103, and the whole-body RF coil 107 housed therein. The hollow bore 1021 is formed in a substantially cylindrical shape into which the subject P such as a patient is moved. More particularly, in the gantry 102, the whole-body RF coil 107 is disposed; the gradient coil 103 is disposed on the outer periphery side of the whole-body RF coil 107; and the static magnetic field magnet 101 is disposed on the outer periphery side of the gradient coil 103.

Meanwhile, in the present embodiment, the term "circle" also covers the meaning of "ellipse". Moreover, in the present embodiment, the term "cylindrical shape" is not limited to imply that the cross-sectional shape orthogonal to the central axis of a cylinder is exactly circular. Thus, the term "cylindrical shape" also includes the case in which the cross-sectional shape orthogonal to the central axis of a cylinder is elliptical.

Moreover, the gantry 102 includes a gantry camera 1022 and a first illuminating unit 1023. The gantry camera 1022 takes images of the hollow bore 1021 of the gantry 102.

Thus, the gantry camera 1022 is used to take images of the subject P who has been inserted inside the hollow bore 1021. After taking images of the hollow bore 1021, the gantry camera 1022 sends the obtained image data to the calculator system 130. For example, the image data obtained by the gantry camera 1022 is used in monitoring the fact that the subject P is not moving the head region when the magnetic resonance imaging apparatus 100 performs imaging of the head region.

The first illuminating unit 1023 is installed in the gantry 102, and is used for illuminating the hollow bore 1021 into which the subject P has been inserted. Inside the hollow bore 1021, the first illuminating unit 1023 is placed along the insertion direction of the subject P who is present on a table-top 1051. For example, the first illuminating unit 1023 represents light emitting diodes (LEDs) arranged along the insertion direction of the subject P. Moreover, the first illuminating unit 1023 is disposed above the eyes of the subject P who has been inserted inside the hollow bore 1021.

The gradient coil 103 is a coil formed in a substantially cylindrical shape of the hollow bore 1021, and is disposed on the inside of the static magnetic field magnet 101. The gradient coil 103 is formed by combining three coils corresponding to the X, Y, and Z axes that are mutually orthogonal; and those three coils individually receive the supply of an electric current from the gradient field power source 104 and generate gradient fields in which the magnetic field intensity changes along the X, Y, and Z axes, respectively. The gradient field power source 104 supplies an electric current to the gradient coil 103 under the control of the sequence control circuitry 120.

The table 105 includes the table-top 1051 on which the subject P is asked to lie down. Under the control of the table control circuitry 106; the table-top 1051, on which the subject P such as a patient is lying down, is inserted inside the imaging opening. That is, the table-top 1051 of the table 105 having the subject P lying thereon is inserted inside the hollow bore 1021. Under the control of the calculator system 130, the table control circuitry 106 drives the table 105 and moves the table-top 1051 in the longitudinal direction and the vertical direction.

A table camera 1052 takes images of the subject P who is lying down on the table-top 1051. For example, the table camera 1052 takes images of the subject P who is yet to be inserted inside the hollow bore 1021. After taking images of the subject P who is lying down on the table-top 1051, the table camera 1052 sends the obtained images data to the calculator system 130. For example, the image data of the images taken by the table camera 1052 is used in identifying the posture of the subject P who is lying down on the table-top 1051. More particularly, the image data of the images taken by the table camera 1052 is used in identifying the position of the head region of the subject P on the table-top 1051, or identifying the posture of the subject P such as whether the subject P is lying in a supine position, or lying on the right side, or lying on the left side. The table camera 1052 is installed, for example, at the ceiling of the imaging room. However, the installation position of the table camera 1052 is not limited to the ceiling. Meanwhile, in order to identify the position of the head region of the subject P, or to identify the posture of the subject P such as whether the subject P is lying in a supine position, or lying on the right side, or lying on the left side; it is alternatively possible to use the image data obtained by the gantry camera 1022.

The whole-body RF coil 107 is a coil of the whole-body type that surrounds the whole body of the subject P. The whole-body RF coil 107 is disposed on the inner periphery side of the gradient coil 103; and applies an RF magnetic field onto the subject P present in the imaging space and receives magnetic resonance signals coming from the subject P due to the impact of the RF magnetic field. More particularly, the whole-body RF coil 107 is formed in a substantially cylindrical shape of the hollow bore 1021; and, based on the RF pulse signals supplied from the transmission circuitry 108, applies an RF magnetic field onto the subject P who is present in the imaging space formed on the inner periphery side of the whole-body RF coil 107. Moreover, the whole-body RF coil 107 receives magnetic resonance signals (MR signals) coming from the subject P due to the impact of the RF magnetic field, and outputs the magnetic resonance signals to the receiving circuitry 110.

The topical RF coil 109 receives the magnetic resonance signals coming from the subject P. More particularly, the topical RF coil 109 caters to all body parts of the subject P and, during the imaging of the subject P, is disposed close to the surface of the target body part for imaging. Then, the topical RF coil 109 receives the magnetic resonance signals coming from the subject P due to the impact of the RF magnetic field applied by the whole-body RF coil 107, and outputs the magnetic resonance signals to the receiving circuitry 110.

The topical RF coil 109 can also have the functionality of a transmission coil that applies an RF magnetic field onto the subject P. In that case, the topical RF coil 109 is connected to the transmission circuitry 108, and applies an RF magnetic field onto the subject P based on the RF pulse signals supplied from the transmission circuitry 108.

The transmission circuitry 108 supplies RF pulses to the whole-body RF coil 107 under the control of the sequence control circuitry 120.

The receiving circuitry 110 performs analog-to-digital (AD) conversion of the analog MR signals output from the whole-body RF coil 107 or the topical RF coil 109; and generates MR data. Then, the receiving circuitry 110 sends the MR data to the sequence control circuitry 120. Meanwhile, AD conversion can be alternatively performed in the whole-body RF coil 107 or the topical RF coil 109. Moreover, the receiving circuitry 110 is also capable of performing other arbitrary signal processing other than AD conversion.

The sequence control circuitry 120 drives the gradient field power source 104, the transmission circuitry 108, and the receiving circuitry 110 based on sequence information sent from the calculator system 130; and performs imaging of the subject P.

Herein, the sequence information represents information in which the sequence for performing the imaging is defined. In the sequence information, the following information is defined: the intensity and the supply timing of the electric current supplied from the gradient field power source 104 to the gradient coil 103; the intensity and the application timing of the RF pulses supplied from the transmission circuitry 108 to the whole-body RF coil 107; and the timing of detection of the MR signals by the receiving circuitry 110. However, the sequence information differs according to the range of the target region for imaging in the body of the subject P.

The sequence control circuitry 120 can be implemented using a processor, or can be implemented using a combination of software and hardware.

As a result of performing imaging of the subject P by driving the gradient field power source 104, the transmission circuitry 108, and the receiving circuitry 110; the sequence control circuitry 120 receives MR data from the receiving circuitry 110 and transfers it to the calculator system 130.

The calculator system 130 performs overall control of the magnetic resonance imaging apparatus 100, and generates MR images. As illustrated in FIG. 1, the calculator system 130 includes a network (NW) interface 131, a memory 132, processing circuitry 133, an input interface 134, and a display 135.

The NW interface 131 performs communication with the sequence control circuitry 120 and the table control circuitry 106. For example, the NW interface 131 sends the sequence information to the sequence control circuitry 120. Moreover, the NW interface 131 receives the MR data from the sequence control circuitry 120.

The memory 132 is used to store the following: the MR data received by the NW interface 131; k-space data placed in the k-space by the processing circuitry 133 (explained later); and image data generated by the processing circuitry 133. The memory 132 is, for example, a semiconductor memory device such as a random access memory (RAM) or a flash memory; or a hard disk; or an optical disk. Meanwhile, the memory 132 can alternatively be installed on the outside of the magnetic resonance imaging apparatus 100.

The input interface 134 receives input of various instructions or information from the operator. The input interface 134 is, for example, a trackball; switch buttons; a mouse; a keyboard; a touchpad that enables performing an input operation by touching an operation screen; a touch-sensitive screen in which a display screen and a touchpad are integrated; a contactless input circuit in which an optical sensor is used; or a voice input circuit. The input interface 134 is connected to the processing circuitry 133; and converts the input operation received from the operator into electrical signals and outputs the electrical signals to the processing circuitry 133. Meanwhile, in the present written description, the input interface 134 is not limited to include a physical operating component such as a mouse or a keyboard. Alternatively, as an example of the input interface 134, it is possible to use an electrical signal processing circuit that receives electrical signals corresponding to an input operation from an external input device installed separately from the calculator system 130, and that outputs the electrical signals to a control circuit.

The display 135 displays the following under the control of the processing circuitry 133: a graphical user interface (GUI) meant for receiving input of imaging conditions; and magnetic resonance images generated by the processing circuitry 133. The display 135 is, for example, a display device such as a liquid crystal display. Herein, the display 135 represents an example of a display unit. Meanwhile, the display 135 can alternatively be installed on the outside of the magnetic resonance imaging apparatus 100.

The processing circuitry 133 performs overall control of the magnetic resonance imaging apparatus 100. More specifically, as an example, the processing circuitry 133 includes an examination information obtaining function 1331, an image data obtaining function 1332, a transportation amount obtaining function 1333, a position identification function 1334, a table-top control function 1335, and an illumination control function 1336.

Herein, for example, the constituent elements of the processing circuitry 133, such as the examination information obtaining function 1331, the image data obtaining function 1332, the transportation amount obtaining function 1333, the position identification function 1334, the table-top control function 1335, and the illumination control function 1336 are stored in the form of computer-executable programs in the memory 132. Moreover, the processing circuitry 133 is a processor. Thus, for example, the processing circuitry 133 reads the computer programs from the memory 132 and executes them so as to implement the functions corresponding to the computer programs. In other words, after having read those computer programs, the processing circuitry 133 gets equipped with the functions illustrated in the processing circuitry 133 in FIG. 1. Meanwhile, with reference to FIG. 1, the processing functions such as the examination information obtaining function 1331, the image data obtaining function 1332, the transportation amount obtaining function 1333, the position identification function 1334, the table-top control function 1335, and the illumination control function 1336 are implemented in a single processor. However, alternatively, the processing circuitry 133 can be configured by combining a plurality of independent processors, and each processor can execute computer programs and implement the functions. Moreover, with reference to FIG. 1, the computer programs corresponding to the processing functions are stored in a single memory 132. However, alternatively, a plurality of memory circuits can be disposed in a dispersed manner, and the processing circuitry 133 can read computer programs from individual memory circuits.

Meanwhile, the term "processor" used in the explanation implies, for example, a central processing unit (CPU), or a graphics processing unit (GPU), or an application specific integrated circuitry (ASIC), or a programmable logic device (such as a simple programmable logic device (SPLD), or a complex programmable logic device (CPLD), or a field programmable gate array (FPGA)). The processor reads the computer programs stored in the memory 132, and executes them. However, instead of storing the computer programs in the memory 132, they can be directly incorporated into the circuitry of a processor. In that case, the processor reads the computer programs incorporated in the circuitry and executes them so that the functions get implemented.

The examination information obtaining function 1331 obtains examination information that indicates the details of the examination performed with respect to the subject P using the magnetic resonance imaging apparatus 100. The examination information contains information indicating the imaging region of the subject P. Moreover, the examination information can also contain information indicating the posture of the subject P on the table-top 1051.

The image data obtaining function 1332 obtains image data of the images of the subject P, who is lying down on the table-top 1051, taken by the table camera 1052.

The transportation amount obtaining function 1333 obtains the amount of transportation of the table-top 1051. For example, based on the examination information indicating the examination region of the subject P, the transportation amount obtaining function 1333 obtains the amount of transportation of the table-top 1051 until the examination region of the subject P reaches the center of the magnetic field. Alternatively, when an operation for moving the table-top 1051, on which the subject P is present, is received from a healthcare professional such as a technologist, the transportation amount obtaining function 1333 obtains the amount of transportation of the table-top 1051 according to the operation. Meanwhile, the transportation amount obtaining function 1333 recognizes the examination region from the image data of the images taken by the table camera 1052, and can obtain the amount of transportation required for bringing the table-top 1051 to the center of the magnetic field.

The table-top control function 1335 controls the transportation of the table-top 1051. More specifically, the table-top control function 1335 inserts the table-top 1051 inside the hollow bore 1021. For example, the table-top control function 1335 controls the transportation of the table-top 1051 based on the amount of transportation of the table-top 1051 as obtained by the transportation amount obtaining function 1333.

The position identification function 1334 identifies the position of a predetermined region of the subject P who has been inserted inside the hollow bore 1021. The position identification function 1334 represents an example of an identifying unit. The predetermined region is, for example, a set region representing a body region set in the subject P. As an example, the eyes of the subject P represent the set region. However, the set region is not limited to the eyes, and alternatively can be the head region, the region between the eyebrows, or some other region. Herein, for example, the position identification function 1334 identifies the positions of the eyes of the subject P who is present inside the hollow bore 1021.

More specifically, based on at least either the examination information indicating the target region for examination of the subject P or the image data obtained as a result of taking images of the subject P who is present on the table-top 1051, the position identification function 1334 identifies the position of the set region of the subject P who has been inserted inside the hollow bore 1021.

For example, based on the amount of transportation of the table-top 1051 required for transporting the target region for examination as specified in the examination information to the center of the magnetic field, and based on the position of the set region of the subject P who is present on the table-top 1051 and who is identified from the image data; the position identification function 1334 identifies the position of the set region of the subject P who has been inserted inside the hollow bore 1021. That is, based on the amount of transportation of the table-top 1051 as obtained by the transportation amount obtaining function 1333, and based on the position of the set region in the image data of the subject P as obtained by the image data obtaining function 1332 according to the images taken by the table camera 1052; the position identification function 1334 identifies the position of the set region of the subject P who has been inserted in the hollow bore 1021.

Figure 2:
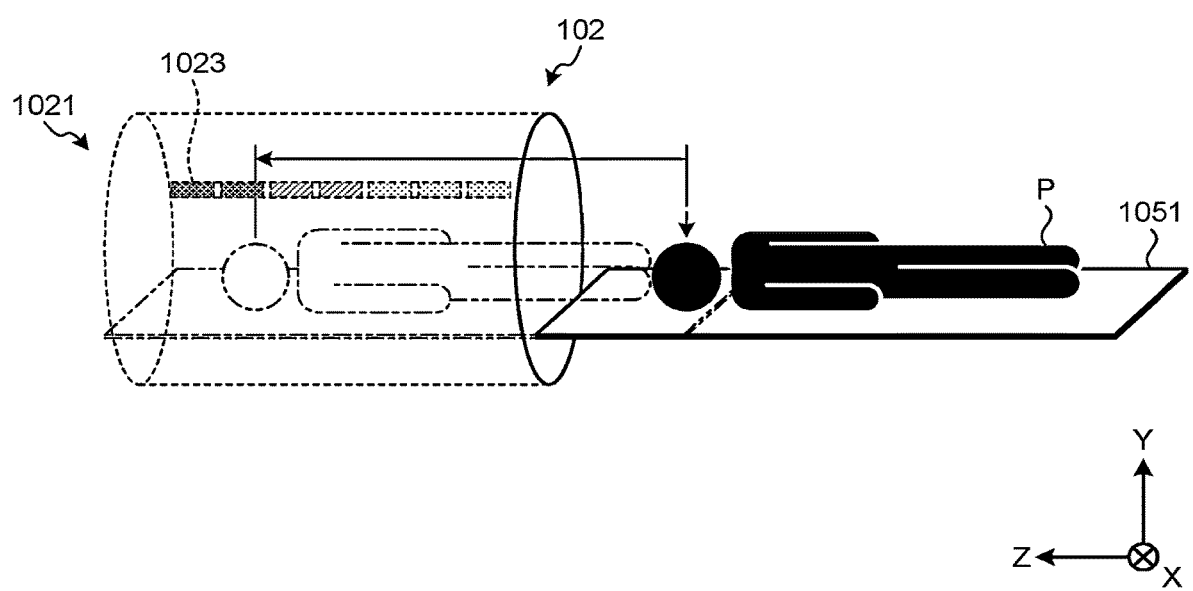
FIG. 2 is a diagram illustrating an example of an identification method for identifying the position of the subject who has been inserted inside a hollow bore.

FIG. 2 is a diagram illustrating an example of an identification method for identifying the position of the set region of the subject P who has been inserted inside the hollow bore 1021. The position identification function 1334 detects the set region of the subject P from the image data of the subject P as obtained by the image data obtaining function 1332 according to the images taken by the table camera 1052. That is, from the image data, the position identification function 1334 identifies the position of the subject P who is present on the table-top 1051 but who is not yet inserted inside the hollow bore 1021. Then, the position identification function 1334 determines that the set region of the subject P who has been inserted inside the hollow bore 1021 is present at the position attained when the set region detected by the image data obtaining function 1332 from the image data moves in the insertion direction by the amount of transportation obtained by the transportation amount obtaining function 1333. Alternatively, the position identification function 1334 can identify the examination region indicated by the examination information from the image data obtained by the image data obtaining function 1332 according to the images taken by the table camera 1052, and can identify the set region based on the information indicating the distance between the set region and the examination region for each body type and based on the identified examination region. That is, the position identification function 1334 either can directly detect the set region from the image data of the images taken by the table camera 1052, or can detect the set region in an indirect manner.

For example, at the time of asking the subject P to lie down on the table-top 1051, if the position for placing the set region is defined; then, instead of having to detect the set region from the image data obtained by the image data obtaining function 1332, the position identification function 1334 can identify the position of the set region of the subject P who has been inserted inside the hollow bore 1021. For example, if a mark or a message indicating the placement position of the head region of the subject P is specified on the table-top 1051, then the subject P places the head region at the specified position. In that case, based on the amount of transportation obtained by the transportation amount obtaining function 1333, the position identification function 1334 identifies the set region of the subject P who has been inserted inside the hollow bore 1021.

The distance from the examination region to the set region of the subject P is fixed in advance according to the body type such as the height of the subject P. For example, when the chest region represents the examination region and the eyes represent the set region, the distance from the chest region to the eyes is fixed in advance according to the body type of the length of the subject P. Such information indicating the distance between the set region and the examination region for each body type is, for example, stored in the memory 132; and the position identification function 1334 identifies the set region based on: the stored information; the examination information indicating the examination region; and the information indicating the body type. The information indicating the body type either can be obtained by the position identification function 1334 using patient identification information included in the examination information, or can be included in the examination information. More particularly, based on the examination region (the imaging region), based on the amount of transportation of the table-top 1051, and based on the body type of the subject P; the position identification function 1334 identifies the position of the set region of the subject P who has been inserted inside the hollow bore 1021. That is, regarding the identification of the position of the set region of the subject P who has been inserted inside the hollow bore 1021, it is not mandatory to use the image data of the images taken by the table camera 1052. If the position of the center of the magnetic field in the device is known and if the premise is that the examination region is carried to the center of the magnetic field; then, instead of having to use the amount of transportation, the position identification function 1334 can use the information indicating the distance between the set region and the examination region and identify the position of the subject P who has been inserted inside the hollow bore 1021. Meanwhile, the position identification function 1334 can identify the examination region, which is indicated by the examination information, from the image data obtained by the image data obtaining function 1332 according to the images taken by the table camera 1052, and then can identify the set region based on the information indicating the distance between the setting region and the examination region for each type and based on the identified examination region.

If the examination region is substantially identical to the set region, then the position of the examination region is same as the position of the set region. Hence, the position identification function 1334 can identify the position of the set region of the subject P, who has been inserted in the hollow bore 1021, without having to use the amount of transportation. For example, if the head region represents the examination region and if the eyes represent the set region, then the position identification function 1334 can determine that the eyes are present at the position of the head region. In that case too, based on the examination information indicating the examination region of the subject P, the position identification function 1334 identifies the position of the set region of the subject P who has been inserted in the hollow bore 1021. Alternatively, when the table 105 is connected to a head coil, the position identification function 1334 determines that the head region represents the examination region.

The illumination control function 1336 controls the illumination state of the first illuminating unit 1023 based on the position of the set region of the subject P as identified by the position identification function 1334. The illumination control function 1336 represents an example an illumination control unit.

Figure 3:
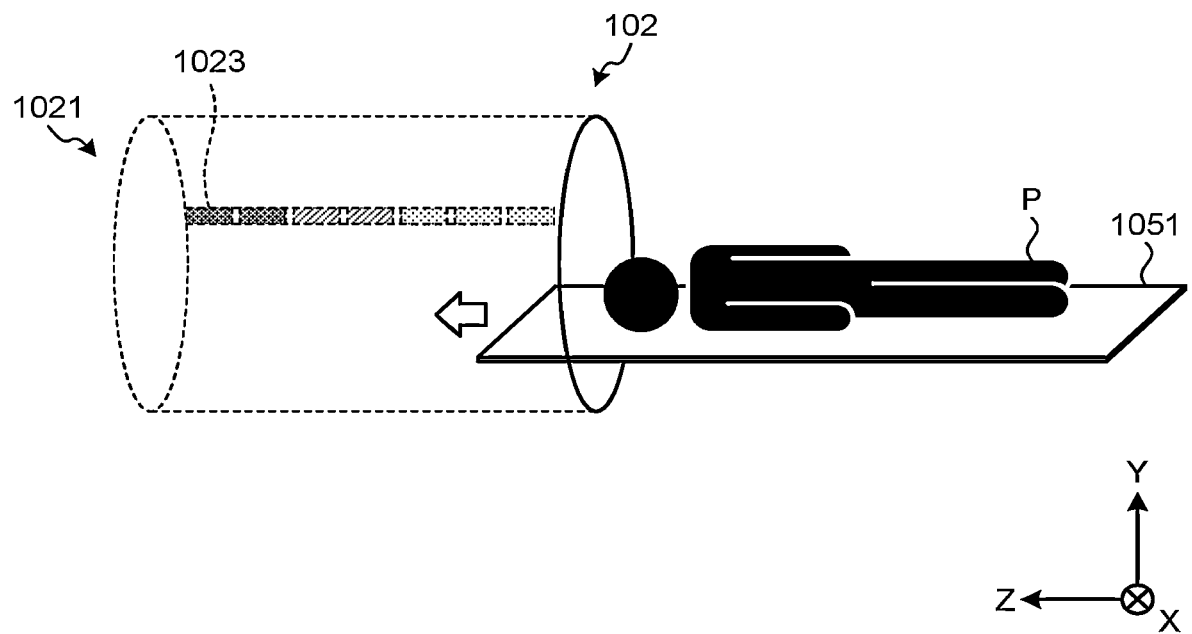
FIG. 3 is a diagram illustrating an example of the lit-up state of a first illuminating unit before the subject is inserted inside the hollow bore.

FIG. 3 is a diagram illustrating an example of the lit-up state of the first illuminating unit 1023 before the subject P is inserted inside the hollow bore 1021 (for example, till the examination region of the subject P is carried to the center of the magnetic field). Before the table-top 1051 is inserted inside the hollow bore 1021 of the gantry 102, the subject P is prone to anxiety about darkness inside the hollow bore 1021. As illustrated in FIG. 3, before the subject P is inserted inside the hollow bore 1021, the illumination control function 1336 activates the first illuminating unit 1023. More specifically, the illumination control function 1336 increases the illumination intensity toward the back of the hollow bore 1021. In this way, as a result of increasing the illumination intensity toward the back of the hollow bore 1021, it becomes possible to apply the savannah effect by which the anxiety about entering the hollow bore 1021 is alleviated.

Figure 4:
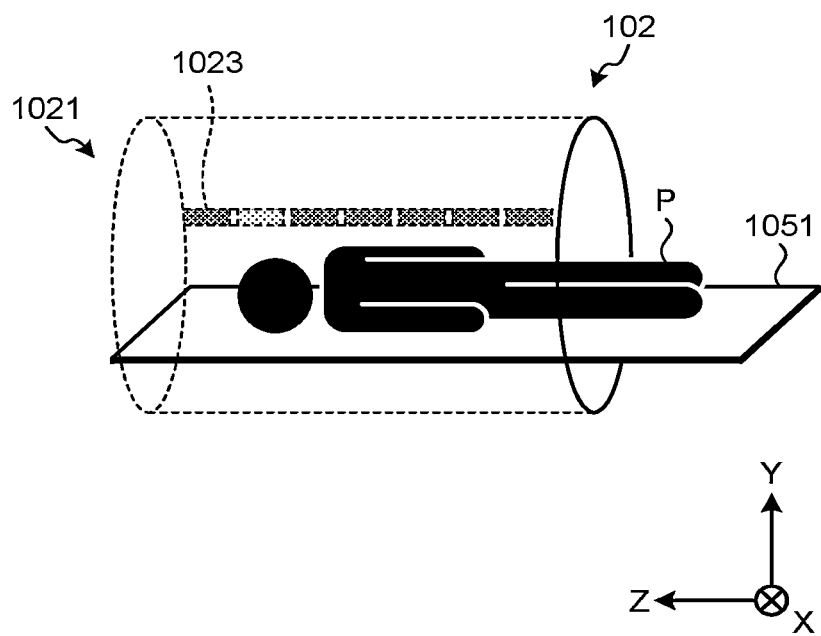
FIG. 4 is a diagram illustrating an example of the lit-up state of the first illuminating unit after the subject has been inserted inside the hollow bore.

FIG. 4 is a diagram illustrating an example of the lit-up state of the first illuminating unit 1023 after the subject P has been inserted inside the hollow bore 1021. As illustrated in FIG. 4, the illumination control function 1336 controls the illumination of the first illuminating unit 1023 corresponding to the position of the set region of the subject P. Meanwhile, sometimes a blanket is put on the subject P. In that case, in order to prevent the blockage of light due to the blanket, the first illuminating unit 1023 is placed at a higher position than the eyes of the subject P. However, since the first illuminating unit 1023 is placed at a higher position than the eyes, the subject P may feel the illumination to be too bright. In that regard, as illustrated in FIG. 4, the illumination control function 1336 lowers the illumination intensity of the first illuminating unit 1023 within a set range from the position of the set region identified by the position identification function 1334. For example, the illumination control function 1336 adjusts the illumination intensity of the first illuminating unit 1023 within a set range to be lower as compared to the illumination intensity of the first illuminating unit 1023 outside the set range. As a result, the illumination control function 1336 becomes able to lessen the feeling of excessive brightness that the subject P has with respect to the first illuminating unit 1023.

The gantry camera 1022 takes images of the subject P who has been inserted inside the hollow bore 1021. When the hollow bore 1021 is dark, the gantry camera 1022 generates dark image data. Moreover, in the case of taking images of the head region of the subject P, a healthcare professional such as a technologist needs to confirm the state of the subject P, such as whether or not the subject P is moving the head region. However, the healthcare professional is not able to confirm the state of the subject P using dark image data. In that regard, when the head region represents the target region for examination, the illumination control function 1336 increases the illumination intensity of the first illuminating unit 1023 within the set range from the position of the set region of the subject P. That is, when the head region represents the target region for examination, the illumination control function 1336 increases the illumination intensity of the first illuminating unit 1023 within the set range from the head region. In this way, by increasing the brightness of the area near the head region of the subject P who is present inside the hollow bore 1021, it becomes possible to hold down a situation in which a healthcare professional is not able to confirm the state of the subject P.

Given below is the explanation of various operations performed by the magnetic resonance imaging apparatus 100.

Figure 5:
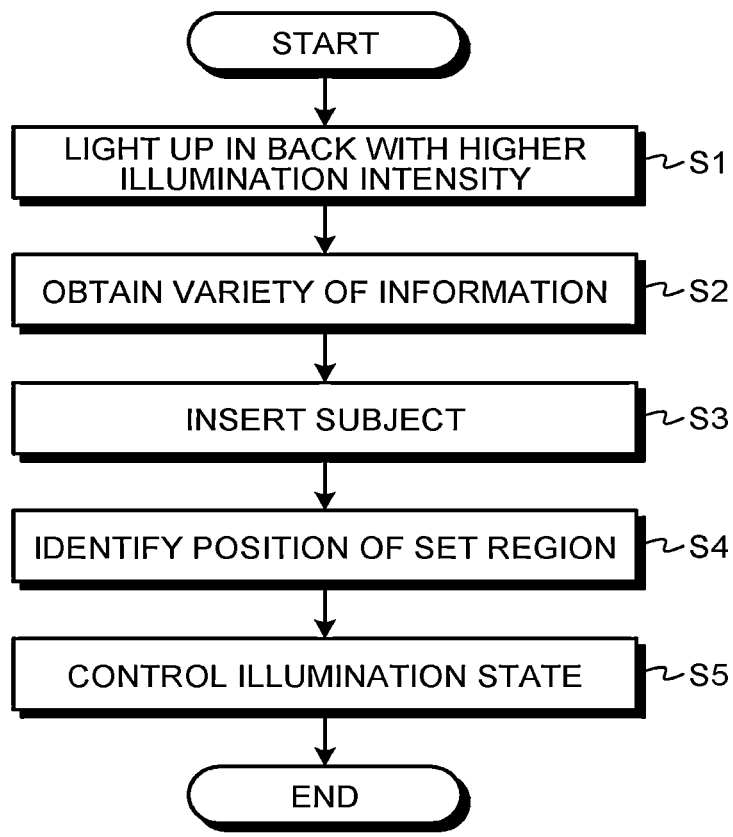
FIG. 5 is a flowchart illustrating an example of an illumination control operation performed by the magnetic resonance imaging apparatus according to the first embodiment.

FIG. 5 is a flowchart illustrating an example of an illumination control operation performed by the magnetic resonance imaging apparatus 100 according to the first embodiment.

The illumination control function 1336 lights up the first illuminating unit 1023 with an increasing illumination intensity toward the back of the hollow bore 1021 (Step S1).

The processing circuitry 133 of the magnetic resonance imaging apparatus 100 obtains a variety of information to be used in identifying the position of the set region of the subject P who is present inside the hollow bore 1021 (Step S2). More specifically, if the examination information indicating the examination region of the subject P is used by the position identification function 1334, then the examination information obtaining function 1331 obtains the examination information. Moreover, if the image data of the subject P present on the table-top 1051 is used, then the image data obtaining function 1332 obtains the image data. Furthermore, if the amount of transportation of the table-top 1051 is used, then the transportation amount obtaining function 1333 obtains the amount of transportation of the table-top 1051. Moreover, if the information indicating the body type of the subject P is used, then the processing circuitry 133 obtains the information indicating the body type.

The table-top control function 1335 inserts the table-top 1051 inside the hollow bore 1021 (Step S3).

The position identification function 1334 identifies the position of the set region of the subject P who is present inside the hollow bore 1021 (Step S4).

The illumination control function 1336 controls the illumination state of the first illuminating unit 1023 based on the position of the set region (Step S5).

With that, the magnetic resonance imaging apparatus 100 ends the illumination control operation.

As explained above, the magnetic resonance imaging apparatus according to the present embodiment includes the first illuminating unit 1023 that illuminates the hollow bore 1021 provided in the gantry 102. Moreover, the magnetic resonance imaging apparatus 100 identifies the position of a predetermined region of the subject P, who has been inserted inside the hollow bore 1021, inside the hollow bore 1021. Then, the magnetic resonance imaging apparatus 100 controls the illumination state of the first illuminating unit 1023 based on the position of the set region. For example, the magnetic resonance imaging apparatus 100 lowers the illumination intensity of the first illuminating unit 1023. That enables achieving reduction in the possibility that the subject P feels too bright due to the first illuminating unit 1023. Hence, the magnetic resonance imaging apparatus 100 can appropriately control the illumination in the hollow bore 1021 of the gantry 102.

First Modification Example

Figure 6:
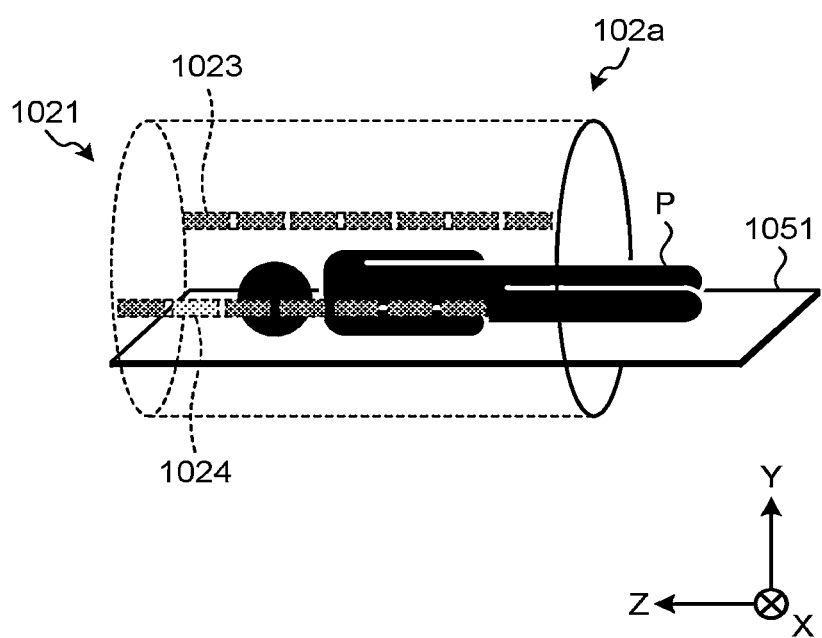
FIG. 6 is a diagram illustrating an example of the arrangement of the first illuminating unit and a second illuminating unit according to a first modification example.

FIG. 6 is a diagram illustrating an example of the arrangement of the first illuminating unit 1023 and a second illuminating unit 1024 according to a first modification example. Inside the hollow bore 1021, a gantry 102a includes the first illuminating unit 1023 on the left side of the subject P who is lying on the table-top 1051 in a supine position, and includes the second illuminating unit 1024 on the right side of the subject P. The second illuminating unit 1024 is meant for illuminating the hollow bore 1021 into which the subject P is moved. On the right side of the subject P who has been inserted inside the hollow bore 1021, the second illuminating unit 1024 is placed along the insertion direction of the subject P. For example, the second illuminating unit 1024 represents LEDs arranged along the insertion direction of the subject P.

Meanwhile, the subject P is not limited to be lying in a supine position, but can also lie on the right side or on the left side. The first illuminating unit 1023 is placed on the left side of the subject P. Hence, if the subject P is lying on the right side, then the first illuminating unit 1023 happens to be behind the subject P. Hence, even when the first illuminating unit 1023 is lit up, the subject P is less likely to feel too bright.

The second illuminating unit 1024 is placed on the right side of the subject P. Hence, if the subject P is lying on the left side, then the second illuminating unit 1024 happens to be behind the subject P. Hence, even when the second illuminating unit 1024 is lit up, the subject P is less likely to feel too bright. In that regard, based on the position of the set region of the subject P and based on the orientation of the subject P, the illumination control function 1336 controls the illumination state of the first illuminating unit 1023 and the second illuminating unit 1024.

More specifically, based on the image data of the images taken by the table camera 1052, the illumination control function 1336 determines whether the subject P is lying on the right side on the table-top 1051 or is lying on the left side on the table-top 1051.

Then, based on the orientation of the subject P as determined by the image data of the images taken by the table camera 1052, the illumination control function 1336 lowers the illumination intensity of the first illuminating unit 1023 or the second illuminating unit 1024 within the set range from the position of the set region of the subject P. Moreover, based on the orientation of the subject P as determined by the image data of the images taken by the table camera 1052, the illumination control function 1336 lights up the first illuminating unit 1023 or the second illuminating unit 1024 within the set range from the position of the set region of the subject P.

That is, if the image data of the images taken by the table camera 1052 indicates that the subject P is lying on the left side, then the illumination intensity of the first illuminating unit 1023 is lowered within the set range of the position of the set region of the subject P, and the second illuminating unit 1024 is lit up within the set range of the position of the set region of the subject P. On the other hand, if the image data of the images taken by the table camera 1052 indicates that the subject P is lying on the right side, then the illumination intensity of the second illuminating unit 1024 is lowered within the set range of the position of the set region of the subject P, and the first illuminating unit 1023 is lit up within the set range of the position of the set region of the subject P.

According to at least one aspect of the embodiment described above, the illumination inside the hollow bore 1021 of the gantry 102 or the gantry 102a can be controlled in an appropriate manner.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
   a gantry that has a hollow bore;
   a first illuminating unit that illuminates the hollow bore; and
   processing circuitry that
      identifies a position of a predetermined region of a subject inside the hollow bore, and
      controls an illumination state of the first illuminating unit based on the identified position of the predetermined region.

2. The magnetic resonance imaging apparatus according to claim 1, wherein
   the first illuminating unit is disposed along an insertion direction of the subject, and
   the processing circuitry controls an illumination intensity of the first illuminating unit according to the position of the predetermined region.

3. The magnetic resonance imaging apparatus according to claim 1, wherein
   based on
      at least either examination information indicating a target region for an examination of the subject
      or image data in which the subject who is present on a table-top is captured,
   the processing circuitry identifies the position of the predetermined region of the subject who has been inserted inside the hollow bore.

4. The magnetic resonance imaging apparatus according to claim 3, wherein
   based on an amount of transportation required for transporting the target region for the examination, which is specified in the examination information, to a center of a magnetic field, and
   based on the position of the predetermined region on the table-top as identified using the image data,
   the processing circuitry identifies the position of the predetermined region of the subject who has been inserted inside the hollow bore.

5. The magnetic resonance imaging apparatus according to claim 1, wherein the processing circuitry lights up the first illuminating unit before the subject is inserted inside the hollow bore.

6. The magnetic resonance imaging apparatus according to claim 1, wherein the processing circuitry lowers an illumination intensity of the first illuminating unit within a set range from the identified position of the predetermined region.

7. The magnetic resonance imaging apparatus according to claim 1, wherein, when a head region represents a target region for examination, the processing circuitry lowers an illumination intensity of the first illuminating unit within a set range from a position of the predetermined region.

8. The magnetic resonance imaging apparatus according to claim 1, further comprising a second illuminating unit that is placed along an insertion direction of the subject, wherein
- the first illuminating unit is placed along the insertion direction of the subject, and
- based on the position of the predetermined region and an orientation of the subject, the processing circuitry controls the illumination state of the first illuminating unit and the second illuminating unit.

9. An illumination control method implemented in a magnetic resonance imaging apparatus that includes
- a gantry having a hollow bore, and
- a first illuminating unit that illuminates the hollow bore, the illumination control method comprising:
- identifying a position of a predetermined region of a subject inside the hollow bore, and
- controlling an illumination state of the first illuminating unit based on the identified position of the predetermined region.

* * * * *